US006237397B1

(12) United States Patent
Shinar et al.

(10) Patent No.: US 6,237,397 B1
(45) Date of Patent: May 29, 2001

(54) CHEMICAL SENSOR AND COATING FOR SAME

(75) Inventors: Ruth Shinar; Guojun Liu; Marc D. Porter, all of Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 09/413,628

(22) Filed: Oct. 6, 1999

(51) Int. Cl.[7] .................................................... G01N 29/02

(52) U.S. Cl. ............... 73/24.06; 73/23.2; 73/31.05; 73/31.01; 73/31.02; 310/313 R

(58) Field of Search .................... 73/23.2, 24.06, 73/31.01, 31.02, 31.03, 31.05; 310/313 R

(56) References Cited

U.S. PATENT DOCUMENTS

| | | | |
|---|---|---|---|
| 4,243,960 | * | 1/1981 | White et al. ...................... 310/313 R |
| 4,381,922 | * | 5/1983 | Frey et al. ........................... 73/23.31 |
| 5,086,286 | * | 2/1992 | Yasukawa et al. ................... 73/23.2 |
| 5,408,999 | * | 4/1995 | Singh et al. .......................... 600/342 |
| 5,820,551 | * | 10/1998 | Hill et al. ............................. 600/347 |
| 6,042,788 | * | 5/2000 | De Wit et al. ..................... 422/82.02 |

OTHER PUBLICATIONS

Modern Practice of Gas Chromatography, Grob, Ed., 1977, pp. 123–125.*
U.S. application No. 60/065,349, Dilger et al., Nov. 12, 1997.
William H. King, Jr., Piezoelectric Sorption Detector, Analytical Chemistry, vol. 36, No. 9, Aug. 1964, pp. 1735–1739.
Jay W. Grate, Stephen J. Martin, and Richard M. White, Acoustic Wave Microsensors Part II, Analytical Chemistry, vol. 65, No. 22, Nov. 15, 1993, pp. 987–996.
Stephen J. Martin and Stephen D. Senturla, Dynamics and Response of Polymer–Coated Surface Acoustic Wave Devices: Effect of Viscoelastic Properties and Film Resonance, Analytical Chemistry, vol. 66, No. 14, Jul. 15, 1994, pp. 2201–2219.
Jay W. Gate and Samuel J. Patrash, Method for Estimating Polymer–Coated Acoustic Wave Vapor Sensor Responses, Jul. 1, 1995, Analytical Chemistry, vol. 67, No. 13, Jul. 1, 1995, pp. 2162–2169.
Edward T. Zellers and Mingwei Han, Effects of Temperature and Humidity on the Performance of Polymer–Coated Surface Acoustic Wave Vapor Sensor Arrays, Analytical Chemistry, vol. 68, No. 14, Jul. 15, 1996, pp. 2409–2418.
Daniel A. Buttry and Michael D. Ward, Measurement of Interfacial Processes at Electrode Surfaces with the Electrochemical Quartz Crystal Microbalance, Chemical Reviews, 1992, vol. 92, No. 6, pp. 1355–1379.

(List continued on next page.)

Primary Examiner—Hezron Williams
Assistant Examiner—Michael Cygan
(74) Attorney, Agent, or Firm—Marshall, O'Toole, Gerstein, Murray & Borun

(57) ABSTRACT

An acoustic wave based-chemical sensor containing a crystal substrate and a coating of small particulate matter is disclosed. The small particulate matter can be graphite particles. Transducers are connected to the crystal substrate to generate an alternating potential across the crystal substrate, which in turn causes the crystal to resonate due to the converse piezoelectric effect. The coating absorbs the analyte, thus changing the mass of the sensor, and accordingly changing its resonant frequency. The transducers detect this change in resonant frequency to indicate that the analyte is present. The use of small particulate matter results in a coating having a large surface area which facilitates mass uptake of large amounts of VOCs, improved acoustic properties even with relatively thick coatings, and a high operational temperature range.

26 Claims, 4 Drawing Sheets

OTHER PUBLICATIONS

K. K. Kanazawa, A General Solution for the Change in Mechanical Resonance of a Quartz Oscillator Due to Visoelastic Overlayers, Apr. 30, 1986, pp. 1–22.

Ralph Lucklum, Carsten Behling, Richard W. Cernosek, and Stephen J. Martin, Determination of Complex Shear Modulus with Thickness Shear Mode Resonators, J. Phys. D: Appl. Phys. 30 1997, pp. 346–356.

\* cited by examiner

CHEMICAL SENSOR AND COATING FOR SAME

FIELD OF THE INVENTION

The present invention generally relates to systems for monitoring environmental contaminants and, more particularly, to systems for monitoring fugitive emissions from process equipment.

BACKGROUND OF THE INVENTION

Industrial plants which handle volatile organic compounds (VOCs) typically experience unwanted emissions of such compounds into the atmosphere from point sources, such as smoke stacks, and non-point sources, such as valves, pumps, and fittings installed in pipes and vessels containing the VOCs. Such VOCs include, but are not limited to, aromatics (e.g., benzene, toluene, ethylbenzene, and xylenes), halogenated hydrocarbons (e.g., carbon tetrachloride, 1,1,1-trichloroethane, and trichloroethylene), ketones (e.g., acetone, and methyl ethyl ketone), alcohols (e.g., methanol, ethanol, and propanol), ethers (e.g., dimethyl ether and methyl t-butyl ether), and aliphatic hydrocarbons (e.g., natural gas and gasoline).

Emissions from non-point sources, referred to as fugitive emissions, typically occur due to the leakage of the VOCs from joints and seals. Fugitive emissions from control valves can occur as the result of leakage through the packing between the valve stem and the body or bonnet of the valve. Valves employed in demanding service conditions involving frequent movement of the valve stem and large temperature fluctuations typically suffer accelerated deterioration of the valve stem packing, which results in greater fugitive emissions than valves employed in less demanding service.

While improvements in valve stem packing materials and designs have reduced fugitive emissions and lengthened the life of valve packing, the monitoring of fugitive emissions has become important as a means to identify and reduce fugitive emissions, and to comply with the more stringent regulation of emissions. For example, the Environmental Protection Agency (EPA) has promulgated regulations for specifying the maximum permitted emission of certain hazardous air pollutants from control valves, and requires periodic surveys of emissions from control valves.

Current methods of monitoring fugitive emissions involve manual procedures using a portable organic vapor analyzer. This manual method is time consuming and expensive to perform, and also can yield inaccurate results due to ineffective collection of the fugitive emissions from the equipment being monitored. If measurements are made on a valve exposed to wind, emissions from the valve may be dissipated before the analyzer can properly measure the concentration of the emissions. Also, if the analyzer is not carefully moved around the valve to capture all the emissions from the valve, an inaccurate measurement will result. Manual measurement methods also require plant personnel to dedicate a significant amount of time to making the measurements, thereby distracting plant personnel from other duties.

Automated monitoring and detection of fugitive emissions can yield significant advantages over existing manual methods. The EPA regulations require surveys of fugitive emissions at periodic intervals. The length of the survey interval can be monthly, quarterly, semi-annually, or annually, with the required surveys becoming less frequent if the facility operator can document a sufficiently low percentage of control valves exhibiting excessive leakage. Thus, achieving a low percentage of leaking valves reduces the number of surveys required per year. In a large industrial facility, where the total number of survey points can range from 50,000 to 200,000, a reduced number of surveys can result in large cost savings. By installing automated fugitive emission-sensing systems on valves subject to the most demanding service conditions, and thus, most likely to develop leaks, compliance with the EPA regulations can be more readily achieved for the entire facility.

However, employing chemical sensors in an industrial environment requires designing sensors that perform satisfactorily in the presence of high relative humidity across a broad temperature range. The sensors must be able to discriminate between the emissions of interest and other environmental contaminants, while retaining sufficient sensitivity to detect low concentrations of the fugitive emissions. A provision also must be made to enable periodic calibration of the sensors. The output signals from the fugitive emission sensing system must be suitable for input into plant monitoring and control systems typically found in process plants. This permits simple and inexpensive integration of the sensing system into existing plant process control systems.

The fugitive emission sensing system must be inexpensive to manufacture, and use a power source that is readily available in a typical process plant in order to keep installation costs to a minimum. The system must be suitable for use in hazardous areas subject to risk of explosion, requiring electrical equipment to be intrinsically safe or of an explosion-proof design. It also must be able to operate in harsh environments, including areas subject to spray washing, high humidity, high and low temperatures, vibration, oxidizing gases, and other gases which affect sensor performance. The system also must be simple and reliable, in order to keep maintenance costs to a minimum.

In certain applications, the sensors used to detect fugitive emissions are provided in the form of piezoelectric-based sensors having high sensitivities to mass changes, such that when an alternating potential is applied across the sensors, changes in resulting wave characteristics in the sensors, specifically the resonant frequency, indicate the presence of the analyte. More specifically, the sensors typically include a quartz crystal substrate with an outer layer made of material selected to most effectively absorb the analyte. Such outer coatings are selected to increase sensitivity, while reducing acoustic wave damping effects. In addition, such materials should be environmentally robust to accommodate the aforementioned wide temperature ranges, humidity ranges, and high levels of dust particles and other contaminants and oxidants.

SUMMARY OF THE INVENTION

In accordance with one aspect of the present invention, a chemical sensor is provided which includes a substrate, at least two electrodes connected to the substrate, and a coating positioned over the substrate and the at least one of the electrodes, wherein the coating comprises small particulate matter.

In accordance with another aspect of the present invention, the small particulate matter can comprise graphite particles, silica particles, fluoropolymer particles, such as TEFLON®, and mixtures thereof In accordance with other aspects of the present invention, the particles have a size of about 0.01 to about 2 microns, and preferably, about 0.03 microns to about 1 micron. The coating can have a thickness of about 0.3 to about 12 microns, and preferably about 0.5 microns to about 9 microns.

In accordance with yet another aspect of the present invention, a coating is provided for an acoustic wave based-chemical sensor wherein the coating is comprised of small particulate matter.

These and other aspects and features of the present invention will become more apparent from the following detailed description when taken in conjunction with the accompanying drawings.

Figure 1:
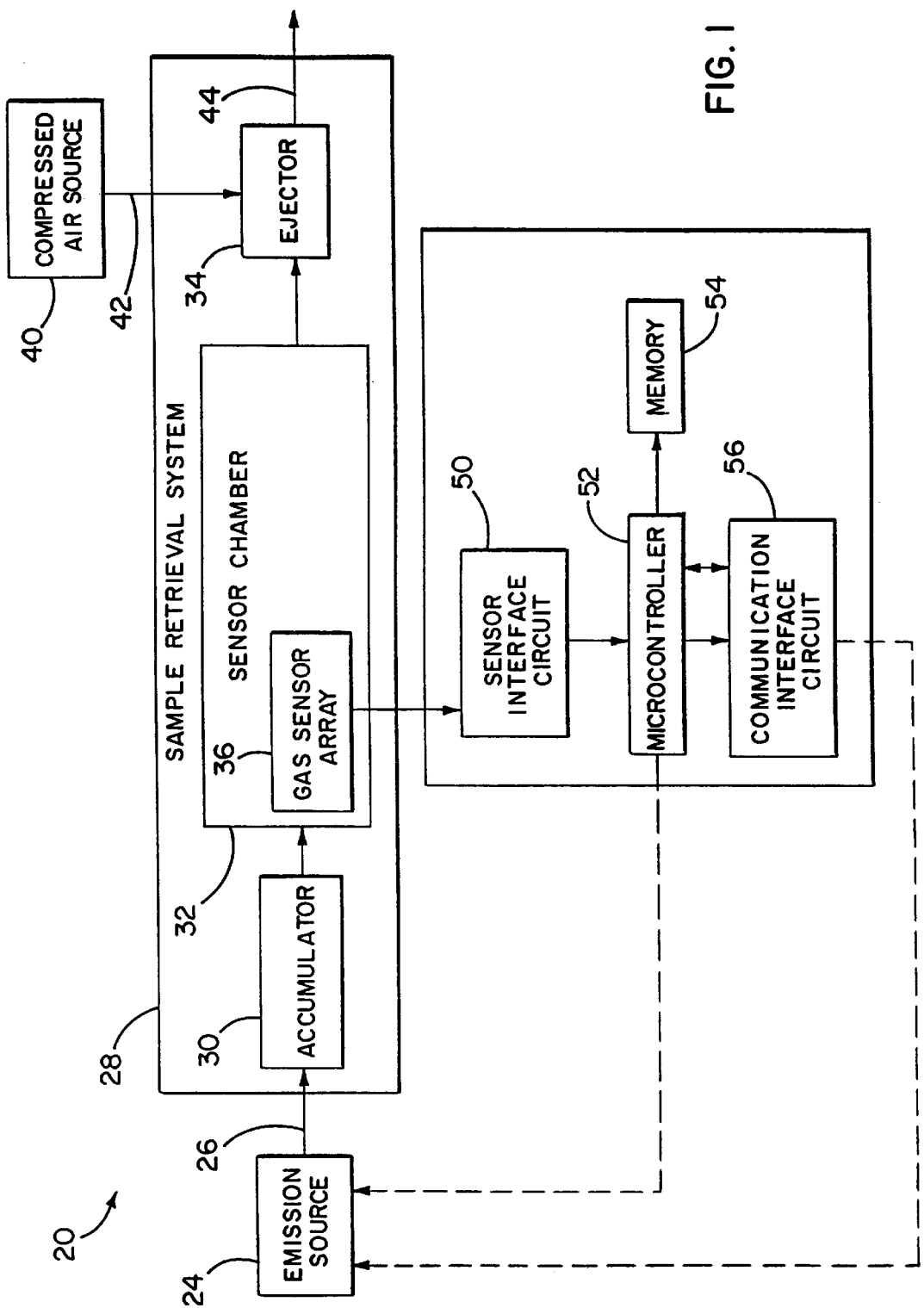
FIG. 1 is a block diagram of a fugitive emissions sensing system employing the present invention.

While the invention is susceptible of various modifications and alternative constructions, certain illustrative embodiments thereof have been shown in the drawings and are described below in detail. It should be understood, however, that there is no intention to limit the invention to the specific examples disclosed, but on the contrary, the intention is to cover all modifications, alternative constructions, and equivalents, falling within the spirit and scope of the invention as defined by the appended claims.

DETAILED DESCRIPTION OF THE INVENTION

Referring now to the drawings, and with specific reference to FIG. 1, a fugitive emissions sensing system utilizing the present invention is generally depicted by reference numeral 20. However, it is to be understood that the present invention is primarily directed to a chemical sensor 22 (FIG. 2) which can be employed in a variety of applications, including applications separate from the fugitive emissions sensing system 20.

Figure 2:
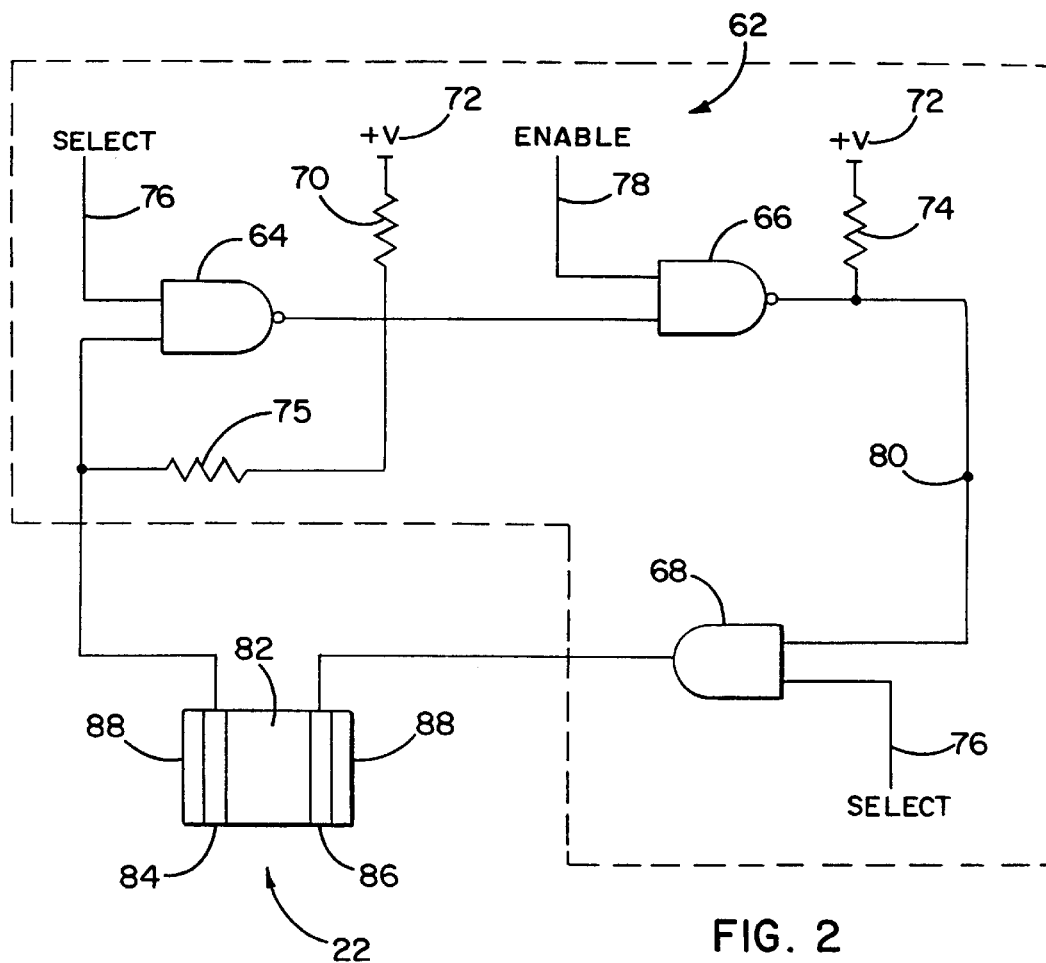
FIG. 2 is a schematic diagram of a chemical sensor circuit including a chemical sensor embodying the present invention.

By way of overview, FIG. 1 is a block diagram of an illustrative fugitive emissions sensing system 20 employing the chemical sensor 22. An emission source 24 is shown, from which a sample stream 26 is drawn into sample retrieval system 28. The sample retrieval system 28 includes an accumulator 30, a sensor chamber 32, and an ejector 34. A chemical sensor array 36 is located within the sensor chamber 32. The sample stream 26 is drawn from the accumulator 30 into the sensor chamber 32, exposing the sensor array 36 to the sample stream 26. The chemical sensor array 36 contains one or more chemical sensors 22 (FIG. 2). The sample stream 26 then passes into the ejector 34. A compressed air source 40 provides compressed air 42 to the ejector 34, creating a pressure drop within the ejector 34 which draws a sample stream 26 through the sensor chamber 32 and into the ejector 34. The compressed air 42 and sample stream 26 are mixed within the ejector 34 and exhausted to atmosphere as a mixture 44.

The chemical sensor array 36 is connected to a sensor interface circuit 50, which processes the signals from the sensor arrays 36 and provides the process signals to a microcontroller 52. The microcontroller 52 stores the data from the sensors 22 in a memory 54, and uses the sensor data received from the fugitive emissions sensing system 20 to initiate control actions to reduce or eliminate the emissions. For example, the microcontroller 52 could close a valve upstream from the emissions source 24 to stop the flow of fluid through the emissions source 24 in order to stop emissions caused by the leakage of the fluid. Alternatively, the microcontroller 52 could alter operating conditions of the emissions source 24 itself to reduce or eliminate the fugitive emissions. The microcontroller 52 may use a communication interface circuit 56 to provide control signals to the upstream valve, the emission source 24, or any other equivalent that may be used to reduce or eliminate the emissions.

It can therefore be seen that the fugitive emissions sensing system 20 may be used to detect the presence of, or measure the concentration of, various types of fluids emitted from the emissions source 24. The system may be used to detect hazardous, toxic or polluting substances emitted from the source, or to detect leakage of non-hazardous substances, the loss of which may be a cause of concern. The fugitive emission sensing system 20 may be used to detect emissions from any kind of source, particularly industrial process equipment from which hazardous substances may leak. Examples include control valves, block valves, pumps installed on lines carrying hazardous gases, agitators, screw conveyors, or other equipment installed on process vessels containing hazardous fluids, heat exchanges, reactors, etc. When emissions are detected by the fugitive emissions sensing system 20, this data may be used by the fugitive emissions sensing system 20 to control the process in such a way as to reduce or eliminate the emissions.

As indicated above, the chemical sensor array 36 may include one or more chemical sensors 22 responsive to a particular analyte or fugitive emission being monitored. In the embodiment depicted in FIG. 2, the chemical sensor 22 is a quartz crystal microbalance (QCM) chemical sensor, but can be another type of piezoelectric acoustic wave devices, including surface acoustic wave (SAW) devices, acoustic plate mode (APM) devices, and flexural plate wave (FPW) devices. Alternatively, fiber optic sensors and electrochemical sensors may be used.

As shown in FIG. 2, the chemical sensor 22 may be connected to an oscillator circuit 62 for monitoring emissions. In an alternative embodiment, the chemical sensor 22 could be connected to a network analyzer. More specifically, the oscillator circuit 62 may include NAND gates 64 and 66, and an AND gate 68, connected in series. A resistor 70 may be connected between the output of the NAND gate 66 and the circuit power supply voltage 72, and a resistor 74 may be connected between the output of NAND gate 66 and circuit power supply voltage 72. A resistor 75 may be connected across the NAND gate 64, connecting a first input to the output. A select signal 76 may be connected to the second input of the NAND gate 64, and the same select signals may also be connected to an input of the AND gate 68. An enable signal 78 may be connected to an input of the NAND gate 66. When the select signal 76 and the enable signal 78 are both high, the NAND gates 64 and 66 act as high-gain inverting amplifiers and cause an oscillator 80 to oscillate between high and low voltage, producing an oscillating square wave output. The oscillating voltage from the oscillator output 80 may be transferred through the AND gate 68 and applied across the sensor 22 casing the sensor 22 to physically resonate.

In order to appreciate the significance of this resonance, it is first important to understand that the chemical sensor 22 utilizes the converse piezoelectric effect. By way of background, the piezoelectric effect holds that a mechanical stress applied to the surfaces of various crystals, including quartz, affords a corresponding electrical potential across the crystal having a magnitude proportional to the applied stress. The electrical charge generated in the quartz crystal under stress is due to the shift of dipoles resulting from the displacement of atoms in the crystalline material. The converse piezoelectric effect holds that application of a voltage across certain crystals, including quartz crystals, results in a corresponding mechanical strain in the crystal. In quartz, this strain or deformation is elastic. It follows that an alternating potential across the crystal causes a vibrational motion in the quartz crystal, i.e., the aforementioned resonance. The chemical sensor 22 therefore includes a crystal substrate 82 which interacts with the oscillating circuit 62, and in turn causes the oscillator circuit 62 to oscillate at the resonant frequency of the chemical sensor 22. Thus, the frequency of the oscillator output 80 will vary as the resonant frequency of the sensor 22 varies.

The resonant frequency of the chemical sensor 22 can vary based on a number of parameters, including the mass, size, shape, and cut of the quartz crystal substrate 82. Quartz crystal exhibits a natural resonant frequency that is a function of the mass and structure of the crystal. The precise size, type of cut, and thickness of the quartz crystal substrate 82 are selected to result in a particular resonant frequency. For example, an AT-cut crystal with a nominal resonant frequency of 8–30 megahertz is suitable for gas sensor applications. Suitable quartz crystal substrates may be obtained from Standard Crystal Corporation of California. Other types of suitable materials to serve as the substrate include lithium niobate ($LiNbO_3$), which is particularly suited for a surface acoustic wave (SAW) based-sensor; and aluminum nitride (AlN), which is particularly suited for a thin film resonator based-sensor.

In order to apply the alternating potential across the substrate 82, first and second electrodes 84 and 86 are connected to the crystal substrate 82 and may be constructed of gold, although other suitable corrosion-resistant and acoustically compatible conductors, possibly including aluminum, palladium, chromium, gold-on-chromium, and graphite, may be used. The electrodes 84 and 86 may serve as both the conductors for generating the alternating current across the crystal substrate 82, and as transducers for sensing parameters related to changes in resonant frequencies resulting in the crystal substrate 82.

As indicated above, the resonant frequency of the chemical sensor 22 is a function of the total mass of the device. Therefore, the mass of any coating provided around the crystal substrate 82 also affects the total mass of the device, and thereby affects the resonant frequency of the chemical sensor 22. The coatings provided about the crystal substrate 82 are selected to absorb molecules of the analyte. When analyte molecules are absorbed by the coating, the mass of the coating is slightly increased, which in turn increases the mass of the entire chemical sensor 22, and thus changes the resonant frequency of the chemical sensor 22. The resonant frequency of the chemical sensor 22 is also a function of the viscoelastic properties of the coatings and mechanical stresses caused by temperature effects in the sensor mounting structure. However, these effects are either negligible or can be compensated for. Thus, a very sensitive detector may be constructed by selecting a coating that has a chemical affinity with the particular analyte of interest. The quantity of analyte molecules absorbed and deposited, and the resulting change in the operating frequency of the oscillator circuit 62, is a function of the concentration of the analyte being measured in the environment surrounding the chemical sensor 22. The frequency changes linearly with changes in analyte concentration, within certain limits.

Thus, a change in the concentration of the analyte of interest may be measured by measuring the change in the frequency of the oscillator output 80. The chemical sensor 22 may be calibrated by exposing the chemical sensor 22 to known concentrations of the analyte and recording the resulting frequency of the oscillator output 80. The chemical sensor 22 may then be used to measure the absolute concentration of the analyte by comparing the measured frequency to the aforementioned recorded values.

The particular coating chosen for the crystal substrate 82 preferably readily absorbs analyte molecules, to provide a high degree of sensitivity to the analyte, but do so without damping the generated waves. The coating also should be functional at elevated temperatures. The present invention provides such a coating in the form of a small particulate matter coating 88.

Low glass transition temperature polymers and some materials with low melting points are attractive as coating materials for such sensors due to their selective, rapid, and reversible responses to volatile organic compounds. However, low glass transition temperature polymers have low shear modulus, and therefore exhibit a relatively large damping effect on acoustic waves. The damping or attenuation of the acoustic waves increases as coating thickness increases, or as ambient temperature increases. This combination of features dictates that coatings of low glass transition temperature polymers be of a limited thickness and be exposed to a limited temperature range. However, since the chemical detection sensitivity of acoustic wave-based sensors is generally proportional to coating thickness, coatings of low glass transition temperature polymers, which are necessarily thin, are accordingly limited in their detection sensitivity. The performance of low melting point materials as coatings generally resembles that of low glass transition temperature polymers. Additionally, the operational temperature range of low melting point materials used as coatings is necessarily limited by the low melting point.

High glass transition temperature polymers exhibit characteristics generally opposite to those of low glass transition temperature polymers when used as chemical sensing coatings. More specifically, since high glass transition temperature polymers have relatively large shear moduli, they exhibit less damping or attenuating effects on acoustic waves over a wide temperature range. Consequently, thicker coatings of high glass transition temperature polymers can be used which in turn increases sensitivity by allowing mass uptake of the analyte. However, high glass transition temperature polymers exhibit extremely slow and hysteresis responses unless used as very thin coatings.

The coating 88 of the present invention results in a coating having all the beneficial properties reference above, i.e., reduced acoustic wave damping or attenuation and a thick coating having a large surface area, thus facilitating the uptake of large volumes of VOCs, fast response times, reversible responses, and operation over a wide temperature range, but without the use of either a high glass transition temperature polymer or a low glass transition temperature polymer and their associated drawbacks. The coating 88 comprises small particulate material that is useful at elevated temperatures, for example, at temperatures of about 50° C. and above, for example up to 200° C., where most polymer coatings cannot be used.

Many materials can be effectively employed as the small particulate matter for the coating 88. Graphite particles are preferred. Other suitable materials include, but are not limited to silica particles, and particles of various fluoropolymers, such as TEFLON® polymers. The small particulate matter comprises particles having a diameter of about 0.01 to about 2 microns, and preferably a diameter of about 0.03 to about 1 micron. The detection sensitivity with regard to VOCs increases as the size of the graphite particle decreases because the smaller size of the particles increases the number of particles in a given volume, thus increasing the surface area of the coating 88, and enabling the uptake of larger amounts of VOC vapor. The open, porous morphology of the coating 88 enables fast and reversible responses to VOCs even when thick coatings are used.

A graphite coating 88 exhibits excellent acoustic properties. Graphite coatings as thick as twelve microns or more, and prepared from small diameter particles, can be used without significant attenuation of acoustic waves, even at elevated temperatures. Moreover, the use of such thick coatings, preferably about 0.5 to about 9 microns, increases detection sensitivity by increasing the amount of VOC absorbed. The hardness of the graphite particles allows for operation at high temperatures, e.g., greater than 50° C. This is in strong contrast to the behavior of the low glass transition temperature polymers and high glass transition temperature polymers discussed above which cannot be used in such high thicknesses or high temperatures because of acoustic damping, or such high thicknesses because of slow response times, respectively.

The coating 88 according to the present invention can be manufactured by using commercially available dispersions of small particulate matter, or by dispersing particles in a solvent or solvents, such as isopropanol or methylene chloride. The graphite particles utilized are preferably about 0.03 micron to about 1 micron in diameter. The graphite particles dispersed in isopropanol then are applied to the substrate 82 and electrodes 84, 86 using a spray technique, although other application techniques, including dipping, can be employed. The substrate is preferably a quartz crystal substrate having a frequency of 9–10 MHZ, and the electrodes 84, 86 are preferably manufactured from chromium/gold. Optionally, the substrate 82 may be placed on a spin coater, a machine adapted to rotate at variable speed, e.g., 500–6000 RPM to evenly distribute the coating 88 at a uniform thickness. A uniform coating thickness is preferably ensured by polishing, although polishing is an optional step. The coating 88 then is annealed at a temperature of about 50° C. to about 100° C. The annealing temperature, most preferably about 60° C. to about 75° C., is important in determining the detection sensitivity, most likely by affecting the surface morphology.

Figure 4:
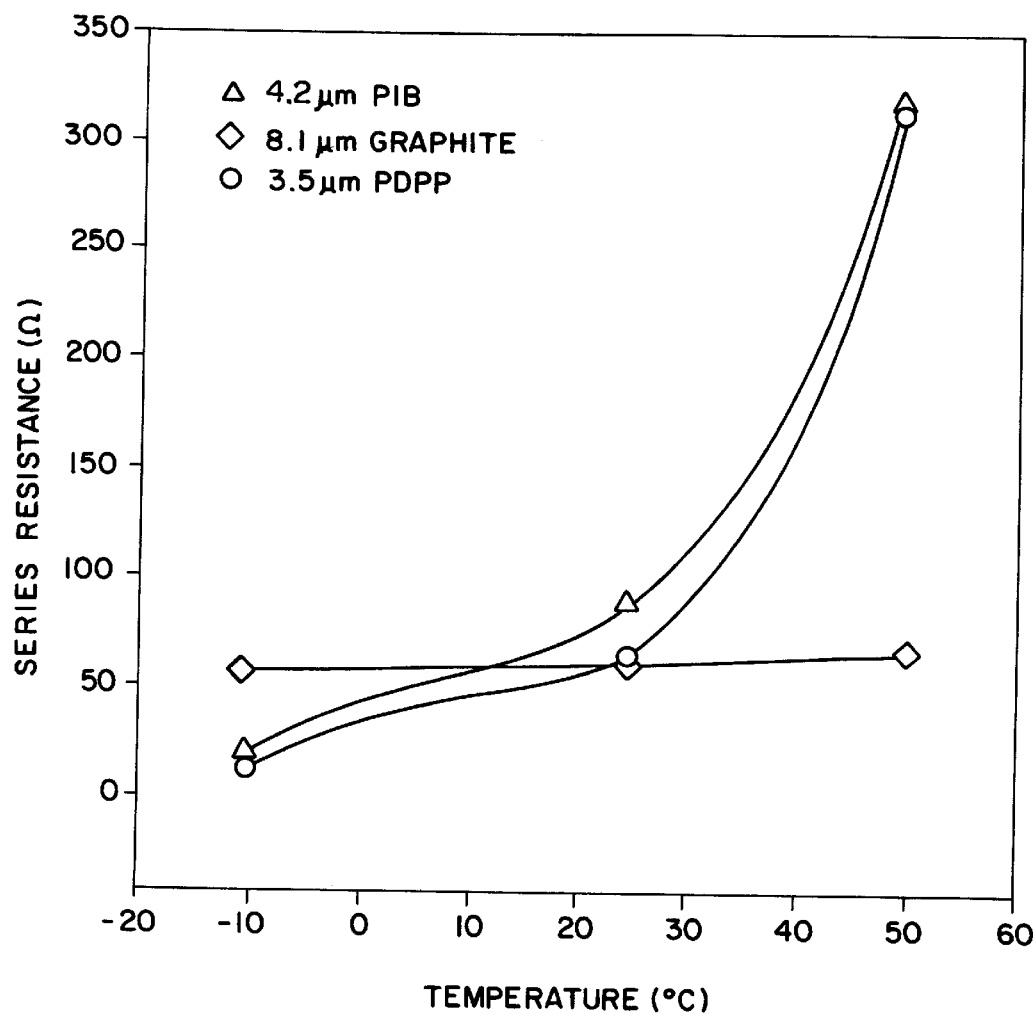
FIG. 4 is a graph plotting series resistance vs. operating temperature.

The resulting coating can be manufactured to a high thickness, e.g., up to twelve microns or more, without significantly attenuating acoustic waves. Moreover, no significant damping of acoustic waves is observed over a temperature range of −10° C. to 50° C. These findings were reached using a network analyzer, measuring the reflection coefficient of the sensor 22 as a function of frequency, in conjunction with equivalent circuit analysis, monitoring the resonant frequency response and other electrical circuit parameters such as series resistance. Acoustic wave damping is indicated when a rise in the series resistance is detected. FIG. 4 shows the series resistance R of a 4.2 micron thick coating of PIB, a 3.5 micron thick coating of PDPP, and a 8.1 micron thick coating of graphite particles over the substrate 82 and the electrodes 84, 86 at temperatures of −10° C., 25° C., and 50° C. As illustrated in FIG. 4, the R values of the PIB and PDPP coatings, unlike that of the graphite coating, strongly increase with increasing temperatures.

Figure 3:
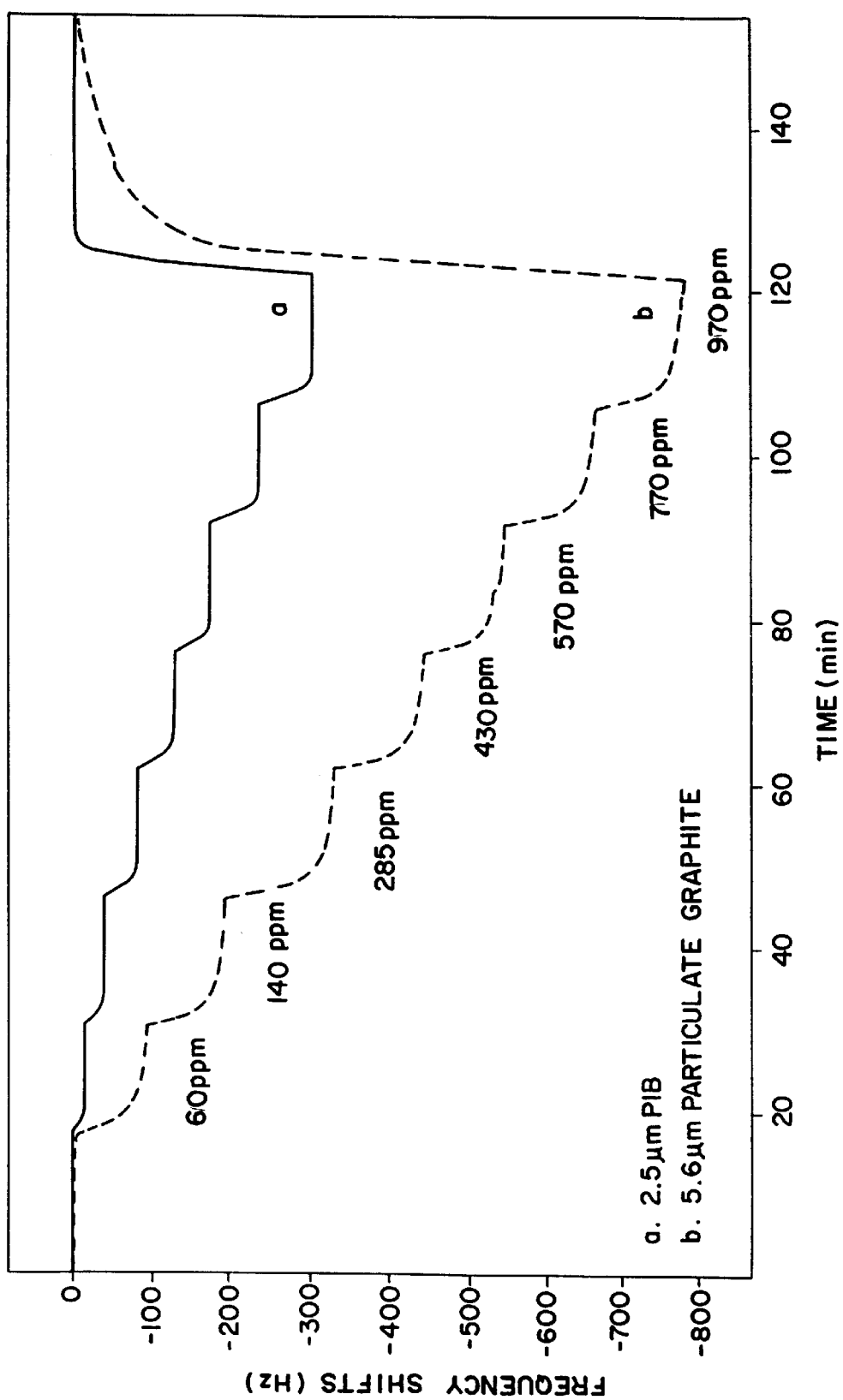
FIG. 3 is a graph plotting frequency response to toluene vs. time.

Moreover, FIG. 3 shows that the responsiveness of a 5.6 micron thick coating of graphite particles is better than a 2.5 micron thick coating of PIB. The actual thickness of the PIB coating is limited because of damping effects at larger thicknesses. The particular test resulting in the plot of FIG. 3 involved toluene as the analyte VOC, at a temperature of 23° C. The toluene response of the graphite coating is linear over the range of 150 to 1000 ppm toluene. The sensitivity appears to be higher at toluene levels below 150 ppm. This may result from a distribution of particle sizes, with an increased sensitivity at the surface of smaller size particles. The response time, i.e., the time required for the response to attain ninety percent of its saturation value, of the coating 88 ranges from about 1 minute to about 9 minutes.

Figure 5:
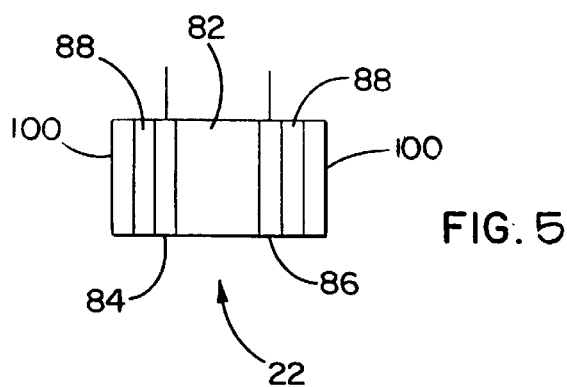
FIG. 5 is a schematic diagram of an alternative embodiment of a chemical sensor according to the present invention.

In an alternative embodiment shown in FIG. 5, a second coating 100 may be positioned over the coating 88. The second coating 100 can be chosen to enhance responsiveness characteristics and detection sensitivity. For example, a second coating that is hydrophobic can reduce interference of water vapor. Graphite coatings with a second layer of hydrophobic poly(isobutylene) or TEFLON showed improved performance at high relative humidities. A second coating that is hydrophilic or contains tailored functional groups, such a amines, carboxylates, of OH groups, can enhance selectivity and specificity in analyte detection. The second coating 100 may be provided at a range of thicknesses, with about 0.2 to about 1.5 microns being preferred.

From the foregoing, it therefore can be seen that the present invention provides an improved acoustic-wave based sensor having a coating of small particulate matter, preferably graphite particles. The graphite coating exhibits excellent acoustic properties which tend not to damp acoustic waves, even at relatively large thicknesses and elevated temperatures, and exhibits excellent responsiveness in terms of volumetric uptake capacity, response time, and reversibility.

What is claimed is:

1. An acoustic wave-based chemical sensor, comprising:
   a substrate;
   at least two electrodes connected to the substrate; and
   a coating positioned over the substrate and at least one of the electrodes, the coating consisting of graphite microparticles.

2. The chemical sensor of claim 1 wherein the graphite microparticles comprises particles having a diameter of about 0.01 to about 2 microns.

3. The chemical sensor of claim 1 wherein the graphite microparticles comprises particles having a diameter of about 0.03 to about 1 micron.

4. The chemical sensor of claim 1 wherein the coating has a thickness of about 0.3 to about 12 microns.

5. The chemical sensor of claim 1 wherein the coating has a thickness of about 0.5 to about 9 microns.

6. The chemical sensor of claim 1 wherein the substrate is selected from the group consisting of quartz crystal, lithium niobate, and aluminum nitrite.

7. The chemical sensor of claim 1 wherein the substrate comprises quartz crystal.

8. The chemical sensor of claim 1 further comprising a a chemically screening overlayer positioned over the coating of graphite microparticles.

9. The chemical sensor of claim 1 wherein the sensor has an operating temperature range of about −10° C. to about 100° C.

10. The chemical sensor of claim 1 wherein the sensor has a response time of about one minute to about nine minutes.

11. The chemical sensor of claim 1 wherein the coating has an open surface morphology.

12. A coating for an acoustic wave based-chemical sensor, the coating consisting of graphite microparticles.

13. The coating of claim 12 wherein the graphite microparticles comprises particles having a diameter of about 0.01 to about 2 microns.

14. The coating of claim 12 wherein the graphite microparticles comprises particles having a diameter of about 0.03 to about 1 micron.

15. The coating of claim 12 wherein the coating has a thickness of about 0.3 to about 12 microns.

16. The coating of claim 12 wherein the coating has a thickness of about 0.5 to about 9 microns.

17. The coating of claim 12 wherein the sensor has an operating temperature range of about −10° C. to about 100° C.

18. The coating of claim 12 wherein the sensor has a response time of about 1 minute to about 9 minutes.

19. A method of detecting volatile organic compounds using an acoustic wave-based chemical sensor comprising:
   a substrate;
   at least two electrodes connected to the substrate; and
   a coating positioned over the substrate and at least one of the electrodes, the coating consisting of graphite microparticles.

20. The method of claim 19 wherein the graphite microparticles comprises particles having a diameter of about 0.01 to about 2 microns.

21. The method of claim 19 wherein the graphite microparticles comprises particles having a diameter of about 0.03 to about 1 micron.

22. The method of claim 19 wherein the coating has a thickness of about 0.3 to about 12 microns.

23. The method of claim 19 wherein the coating has a thickness of about 0.5 to about 9 microns.

24. The method of claim 19 wherein the sensor further comprises a chemically screening overlayer positioned over the coating of graphite microparticles.

25. The method of claim 19 wherein the sensor has an operating temperature range of about −10° C. to about 100° C.

26. The method of claim 19 wherein the sensor has a response time of about one minute to about nine minutes.

* * * * *